(12) United States Patent
Hong

(10) Patent No.: US 12,709,633 B2
(45) Date of Patent: Aug. 18, 2026

(54) WAFER LEVEL CHIP SCALE PACKAGE WITH RHOMBUS SHAPE

(71) Applicants: SILICON MITUS, INC., Seongnam-Si (KR); Silicon-Magic Semiconductor Technology (Hangzhou) Co., Ltd., Hangzhou City (CN)

(72) Inventor: Ji Hoon Hong, Seoul (KR)

(73) Assignees: Silicon Mitus, Inc., Seongnam-Si (KR); Silicon-Magic Semiconductor Technology (Hangzhou) Co., Ltd., Hangzhou (CN)

(*) Notice: Subject to any disclaimer, the term of this patent is extended or adjusted under 35 U.S.C. 154(b) by 443 days.

(21) Appl. No.: 18/343,599

(22) Filed: Jun. 28, 2023

(65) Prior Publication Data

US 2023/0416306 A1 Dec. 28, 2023
US 2024/0317805 A9 Sep. 26, 2024

(30) Foreign Application Priority Data

Jun. 28, 2022 (KR) ........................ 10-2022-0078742

(51) Int. Cl.
*C07K 7/08* (2006.01)
*H10W 99/00* (2026.01)

(52) U.S. Cl.
CPC ............... *C07K 7/08* (2013.01); *H10W 99/00* (2026.01)

(58) Field of Classification Search
CPC ..................... H01L 23/00; H01L 24/14; H01L 2224/14151; H01L 2224/14153; C07K 7/08; H10W 99/00
See application file for complete search history.

(56) References Cited

U.S. PATENT DOCUMENTS

2016/0049176 A1* 2/2016 Lee ........................ G11C 5/063 365/51
2018/0218961 A1* 8/2018 Li ......................... H10W 40/22

FOREIGN PATENT DOCUMENTS

KR 20100047540 A 5/2010
KR 20150116308 A 10/2015

* cited by examiner

*Primary Examiner* — Timor Karimy
(74) *Attorney, Agent, or Firm* — Osha Bergman Watanabe & Burton LLP

(57) ABSTRACT

The present disclosure relates to a wafer level chip scale package with a rhombus shape which includes a semiconductor chip with a rhombus shape and a solder ball array including a plurality of solder balls formed on one surface of the semiconductor chip. Among four interior angles of the semiconductor chip, two of the four interior angles facing each other in a short diagonal direction are approximately 120°, and two of the four interior angles facing each other in a long diagonal direction are approximately 60°.

4 Claims, 5 Drawing Sheets

WAFER LEVEL CHIP SCALE PACKAGE WITH RHOMBUS SHAPE

CROSS-REFERENCE TO RELATED APPLICATION

This application claims priority to Korean Patent Application No. 10-2022-0078742 filed on Jun. 28, 2022 and all the benefits accruing therefrom under 35 U.S.C. § 119, the contents of which are incorporated by reference in their entirety.

BACKGROUND

The present disclosure relates to a wafer level chip scale package with a rhombus shape. More specifically, the present disclosure relates to a wafer level chip scale package with a rhombus shape, which can reduce a chip size by approximately 5 to 12% compared to a conventional rectangular or square chip package, and can still be manufactured using conventional semiconductor manufacturing equipment.

Recently, with the rapid development of portable electronic device such as mobile phones, convergence and complexation between electronic devices are rapidly progressing. For example, in the case of a mobile phone, various functions such as a camera function, an MP3 play function, and a DMB function are becoming complex and being upgraded to high performance.

However, although the portable electronic device should be small and light to be easily carried, this is different from the multi-functionalization and complexation described above. That is, the size of the portable electronic device inevitably increases as multi-functionalization and complexation progresses. As such, there exists a need for miniaturization of parts.

A chip scale package (CSP) refers to a package whose size is approximately 1.2 times the size of a semiconductor chip.

In a general chip scale package manufacturing method, a wafer completed through a semiconductor process is singulated into individual semiconductor chips, and then the individual semiconductor chips are packaged. In line with the trend of miniaturization and mass production of parts, a wafer level chip scale package (WLCSP) is emerging.

The wafer level chip scale package is completed as a package by performing a packaging process in a wafer state to redistribute circuits or performing flip-chip bumping to complete a package structure and then singulating it. Accordingly, the wafer level chip scale package is almost equal to the size of the semiconductor chip and thus is small, and all packaging processes are performed at the wafer level to enable mass production, thereby capable of reducing manufacturing costs.

Meanwhile, according to the prior art, since a method of arranging solder balls on one surface of the semiconductor chip having a rectangular or square shape and then connecting the solder balls to a printed circuit board is applied, there is a limit to reducing the size of the semiconductor chip.

Hereinafter, details will be described with reference to FIGS. 1 and 2.

FIG. 1 is a diagram illustrating a wafer level chip scale package with a square shape according to the prior art, and FIG. 2 is a diagram illustrating a specific and exemplary arrangement of a solder ball array constituting a wafer level chip scale package with a square shape according to the prior art.

Referring to FIGS. 1 and 2, a wafer level chip scale package 1 according to the prior art has a structure in which a solder ball array 3 composed of solder balls arranged to be connected to a printed circuit board is formed on one surface of a semiconductor chip 2 with a square or rectangular shape. In the figures, it is illustrated that there are 16 solder balls, but this is only one non-limiting example.

Respective solder balls constituting the solder ball array 3 should maintain a constant distance from each other to prevent a short circuit with adjacent solder balls, and spacing between solder balls SB1, SB2, SB3, SB4, SB5, SB8, SB9, SB12, SB13, SB14, SB15, and SB16 located on an outer side of the solder ball array 3, and an edge of the semiconductor chip should also be maintained constant.

Therefore, even when the size of a semiconductor die, which is a basic structure of a semiconductor chip, can be reduced by design, the size of the semiconductor chip cannot be reduced due to rules relating to the spacing to be maintained between the solder balls and the spacing to be maintained between the outer solder balls and the edge of the semiconductor chip.

PRIOR ART LITERATURE

Patent Literature

PTL 1: Korean unexamined patent application publication No. 10-2015-0116308 (published date: Oct. 15, 2015, Title: semiconductor package and semiconductor device packaging method)

PTL 2: Korean unexamined patent application publication No. 10-2010-0047540 (published date: May 10, 2010, Title: fan-out wafer level package and its manufacturing method)

SUMMARY

The present disclosure provides a wafer level chip scale package with a rhombus shape that can reduce the chip size by approximately 5 to 12% compared to a conventional rectangular or square chip package.

In addition, the present disclosure provides a wafer level chip scale package with a rhombus shape that can still be manufactured using conventional semiconductor manufacturing equipment.

In accordance with one or more embodiments of the present application, a wafer level chip scale package with a rhombus shape includes a semiconductor chip with a rhombus shape and a solder ball array composed of a plurality of solder balls formed on one surface of the semiconductor chip, in which, among four interior angles of the semiconductor chip, two interior angles facing each other in a short diagonal direction are approximately 120°, and two interior angles facing each other in a long diagonal direction are approximately 60°.

In the wafer level chip scale package with the rhombus shape, separation distances between adjacent solder balls constituting the solder ball array may be the same.

In the wafer level chip scale package with the rhombus shape, the semiconductor chip may have a planar shape formed by two equilateral triangles, and the plurality of solder balls constituting the solder ball array may be symmetrically arranged on the one surface of the semiconductor chip with respect to a short diagonal and a long diagonal of the semiconductor chip.

In the wafer level chip scale package with the rhombus shape, a central point may be located in one of two equilateral triangle regions corresponding to the one surface of the semiconductor chip, and a triangle formed by three line segments connecting three center points of three of the solder balls that are adjacent to each other may be equilateral.

In the wafer level chip scale package with the rhombus shape, n solder balls may be arranged on the short diagonal of the semiconductor chip, and, in upper and lower regions of the short diagonal of the semiconductor chip, the number of solder balls in each row decreasing one by one until the number of solder balls may become one from the n solder balls may be alternately arranged.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
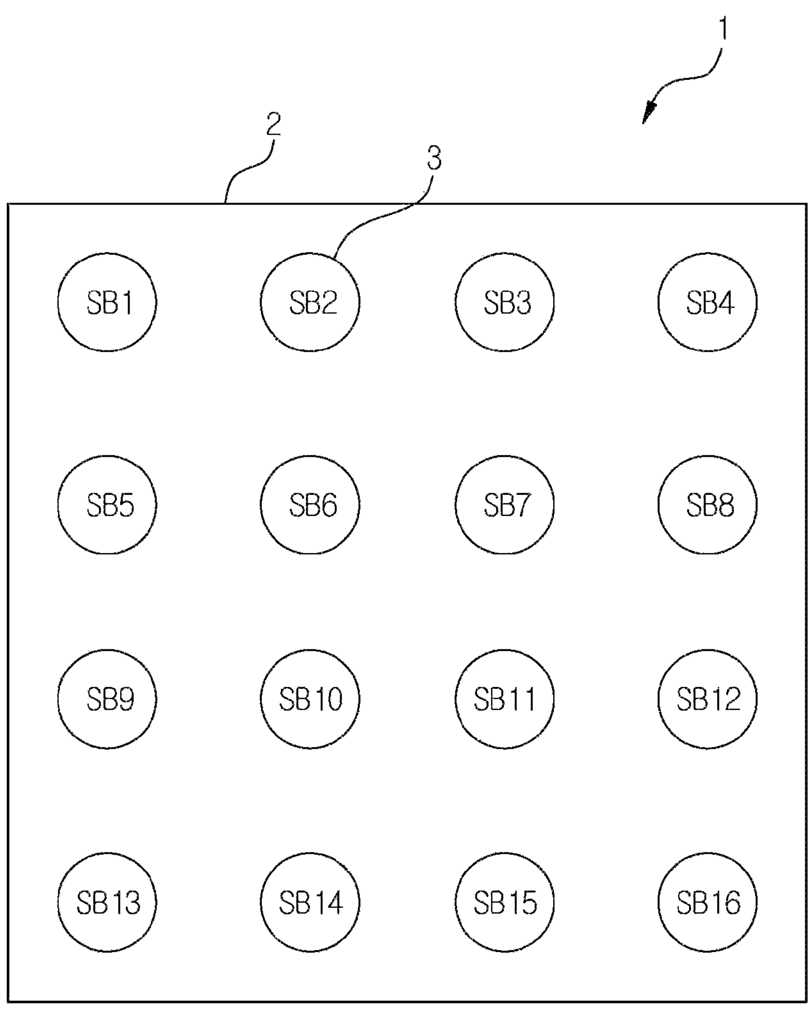
FIG. 1 is a diagram illustrating a wafer level chip scale package with a square shape according to the prior art.

Specific structural or functional descriptions of embodiments according to the concept of the present application disclosed in this specification are only illustrated for the purpose of explaining the embodiments according to the concept of the present application, and the embodiments according to the concept of the present application may be embodied in various forms and should not be construed as limited to the embodiments set forth herein. Rather, these embodiments are provided so that this disclosure will be thorough and complete, and will fully convey the scope of the present application to those skilled in the art.

Various modifications may be made to the embodiments according to the concept of the present application and the embodiments may have various forms, and thus the embodiments are illustrated in the drawings and described in detail in this specification. However, this is not intended to limit the embodiments according to the concept of the present application to specific disclosure forms, and includes all modifications, equivalents, or substitutes included in the spirit and technical scope of the present application.

Unless otherwise defined, all terms used herein, including technical or scientific terms, have the same meaning as commonly understood by one of ordinary skill in the art to which the present application belongs. Terms such as those defined in commonly used dictionaries should be interpreted as having a meaning consistent with the meaning in the context of the prior art, and should not be interpreted in an ideal or excessively formal meaning unless explicitly defined in this specification.

Hereinafter, one or more embodiments of the present application will be described in detail with reference to the accompanying drawings.

Figure 3:
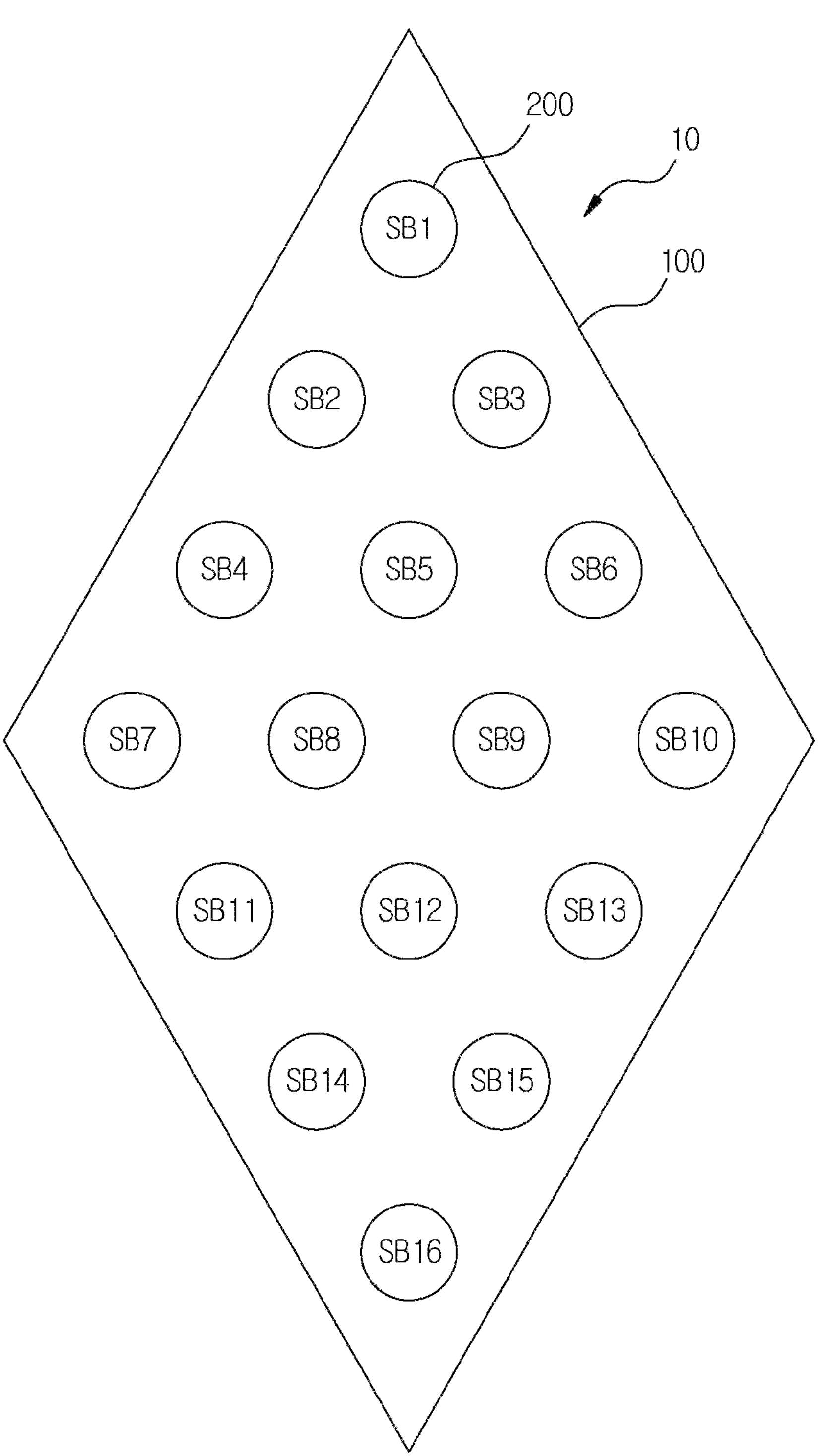
FIG. 3 is a diagram illustrating a wafer level chip scale package with a rhombus shape in accordance with one or more embodiments of the present application.
Figure 4:
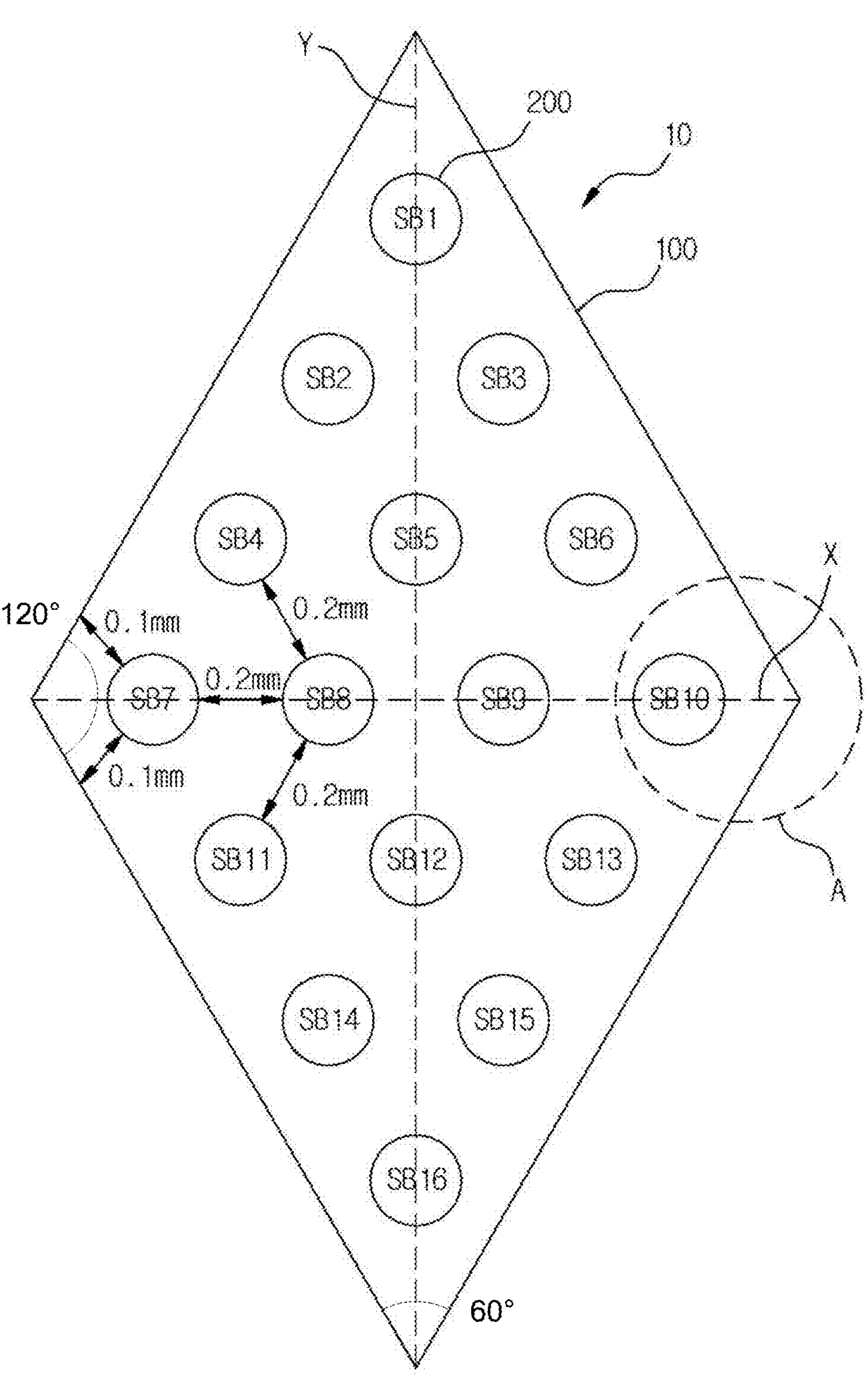
FIG. 4 is a diagram illustrating a specific and exemplary arrangement of solder ball arrays constituting the wafer level chip scale package with the rhombus shape in accordance with one or more embodiments of the present application.
Figure 5:
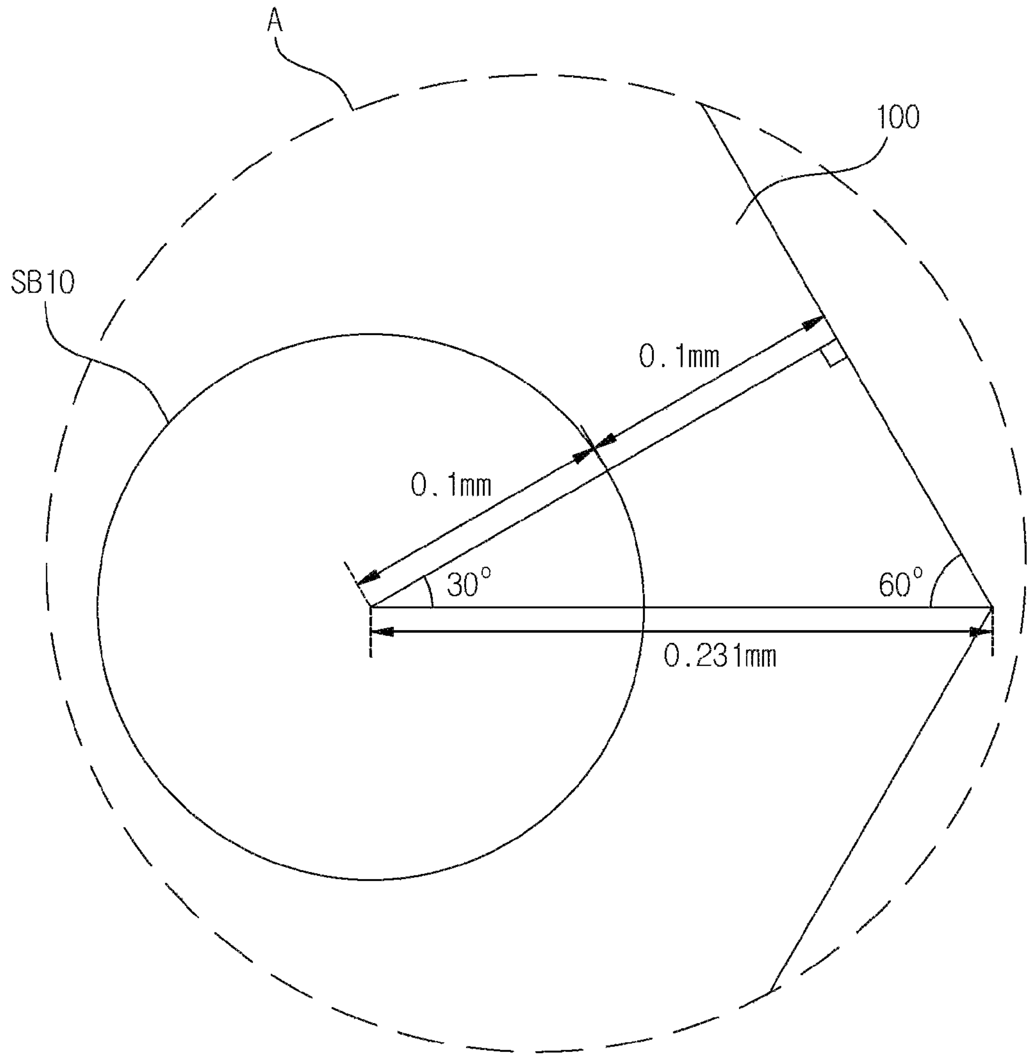
FIG. 5 is a diagram for describing a process of calculating a separation value in a circled corner region of the wafer level chip scale package with the rhombus shape by enlarging part A of FIG. 4.

FIG. 3 is a diagram illustrating a wafer level chip scale package with a rhombus shape in accordance with one or more embodiments of the present disclosure, FIG. 4 is a diagram illustrating a specific and exemplary arrangement of solder ball arrays constituting the wafer level chip scale package with the rhombus shape in accordance with one or more embodiments of the present application, and FIG. 5 is a diagram for describing a process of calculating a separation value in a circled corner region of the wafer level chip scale package with the rhombus shape by enlarging part A of FIG. 4.

Referring to FIGS. 3 to 5, the wafer level chip scale package 10 with a rhombus shape according to one or more embodiments of the present application is configured to include a semiconductor chip with a rhombus shape and a solder ball array composed of a plurality of solder balls formed on one surface of the semiconductor chip, and is configured such that, among four interior angles of the semiconductor chip, two interior angles facing each other in a short diagonal X direction are approximately 120° and two interior angles facing each other in a long diagonal Y direction are approximately 60°.

According to one or more embodiments, the chip size can be reduced by approximately 5 to 12% compared to a conventional rectangular or square chip package.

One or more embodiments are described in more detail as follows.

As described above, according to the prior art, in manufacturing the wafer level chip scale package 1, since a method of connecting the solder balls to the printed circuit board after arranging the solder balls on one surface of the semiconductor chip 2 with a rectangular or square shape is applied, there is a limit to reducing the size of the semiconductor chip 2.

Figure 2:
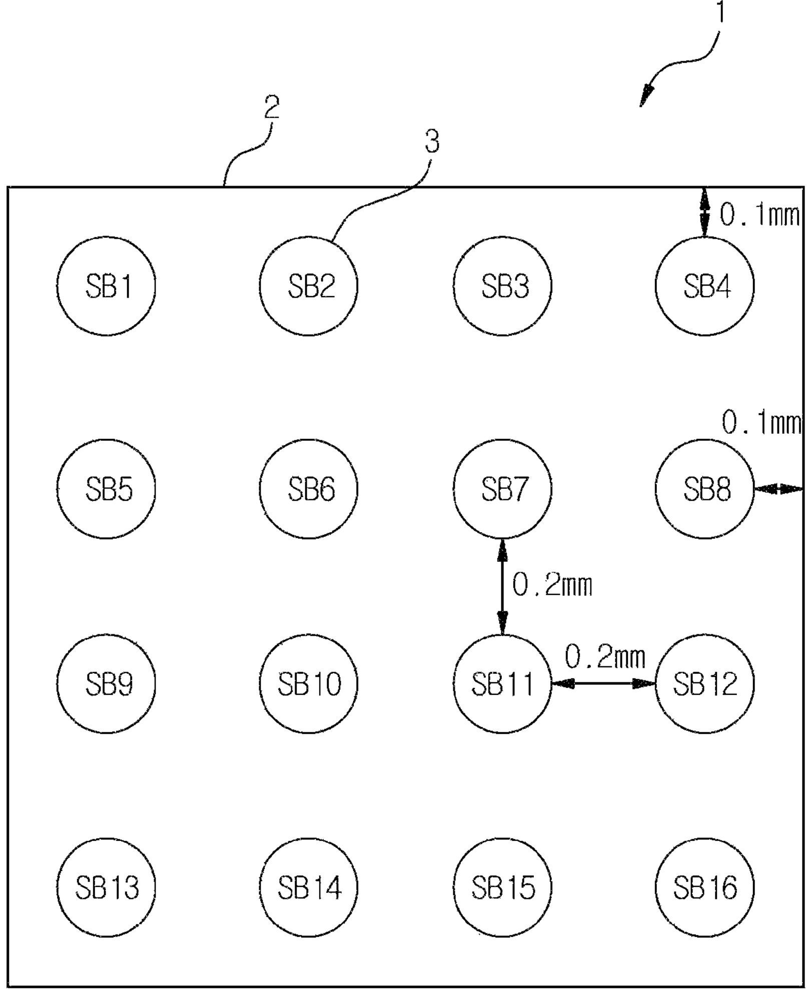
FIG. 2 is a diagram illustrating a specific and exemplary arrangement configuration of a solder ball array constituting the wafer level chip scale package with the square shape according to the prior art.

Hereinafter, details will be described with reference to FIG. 1 illustrating the wafer level chip scale package 1 with the square shape according to the prior art and FIG. 2 illustrating a specific and exemplary arrangement of the solder ball array 3 constituting the wafer level chip scale package 1 with the square shape according to the prior art.

Referring to FIGS. 1 and 2, the wafer level chip scale package 1 according to the prior art comprises the solder ball array 3, which is composed of solder balls arranged to be connected to the printed circuit board and is formed on one surface of the semiconductor chip 2 having a square shape. In the figures, it is illustrated that there are approximately 16 solder balls, but this is only a non-limiting example, and the semiconductor chip 2 may be configured to have a rectangular shape.

Respective solder balls constituting the solder ball array 3 may be disposed at constant spacings from each other to prevent a short circuit with adjacent solder balls, and spacings between each of the solder balls SB1, SB2, SB3, SB4, SB5, SB8, SB9, SB412, SB13, SB14, SB15, and SB16 located on an outer side of the solder ball array 3, and the edge of the semiconductor chip may also be constant.

In the figures, it is general standards that the diameter of the solder balls is approximately 0.2 mm, the spacing between the solder balls is approximately 0.2 mm, and the spacing between the solder balls SB1, SB2, SB3, SB4, SB5, SB8, SB9, SB412, SB13, SB14, SB15, and SB16 located on the outer side thereof and the edge of the semiconductor chip is approximately 0.1 mm. These numerical values are values that may vary somewhat depending on the type of chip, etc., but are currently generally required standards.

Therefore, even when the size of a semiconductor die, which is a basic structure of a semiconductor chip, can be reduced by design, the size of the semiconductor chip cannot be reduced due to rules relating to the spacing to be maintained between the solder balls and the spacing to be maintained between the outer solder balls and the edge of the semiconductor chip.

One or more embodiments of the present application include a semiconductor chip 100 with a rhombus shape and a solder ball array 200 composed of a plurality of solder balls SB1, SB2, SB3, . . . formed on one surface of the semiconductor chip 100, and is configured such that, among four interior angles of the semiconductor chip 100, two interior angles facing each other in a short diagonal X direction are approximately 120°, and two interior angles facing each other in a long diagonal Y direction are approximately 60°.

According to one or more embodiments of the present application, the wafer level chip scale package with the rhombus shape can reduce the chip size by approximately 5 to 12% compared to a conventional rectangular or square chip package and can still be manufactured using conventional semiconductor manufacturing equipment.

For example, separation distances between the respective solder balls constituting the solder ball array 200 may be the same.

For example, the semiconductor chip 100 may have a planar shape in which two equilateral triangles are combined. The plurality of solder balls constituting the solder ball array 200 are symmetrically arranged on one surface of the semiconductor chip 100 with respect to a short diagonal X and a long diagonal Y of the semiconductor chip 100. Three line segments connecting center points of three solder balls adjacent to each other form an equilateral triangle. In addition, n solder balls may be arranged on the short diagonal of the semiconductor chip 100, and, in upper and lower regions of the short diagonal of the semiconductor chip, the number of solder balls in each row decreasing one by one until the number of solder balls becomes one from n solder balls is alternately arranged.

Hereinafter, one or more embodiments for proving chip size reduction will be described.

In the verification example below, the diameter of the solder balls is approximately 0.2 mm, the spacing between the solder balls is approximately 0.2 mm, and the spacing between the solder balls SB1, SB2, SB3, SB4, SB6, SB7, SB10, SB11, SB13, SB14, SB15, and SB16 located on an outer side thereof and the edges of the semiconductor chip, that is, four sides of the rhombus is approximately 0.1 mm.

As illustrated in FIGS. 4 and 5, the semiconductor chip 100 constituting the wafer level chip scale package 10 according to one or more embodiments of the present application has a rhombus shape, and, among four interior angles of the semiconductor chip 100, two interior angles facing each other in the short diagonal X direction are approximately 120°, and two interior angles facing each other in the long diagonal Y direction are approximately 60°.

In particular, FIGS. 4 and 5 disclose a process of calculating a value of separation distance in the circled corner region of the wafer level chip scale package with the rhombus shape according to the present application.

Referring to FIGS. 4 and 5, the number of solder balls constituting the solder ball array 200 is approximately 16, and since a radius of the solder ball SB10 located in the circled corner region of the short diagonal X is approximately 0.1 mm and the spacing between the solder ball SB10 and the edge of the semiconductor chip 100 (i.e., one side of the rhombus) is approximately 0.1 mm, a length of one side of a corner triangle (i.e., a shortest distance from a center of the solder ball SB10 to the edge of the semiconductor chip 100) is approximately 0.2 mm. In addition, the length of a hypotenuse of the corner triangle (i.e., a distance from the center of the solder ball SB10 to a nearest vertex of the semiconductor chip 100) is approximately 0.2/cos 30°=0.231 mm.

Therefore, the length of one side of the equilateral triangle is approximately 0.4 mm×3+2×0.231=1.662 mm.

The area of one equilateral triangle is approximately $\sqrt{3}\times1.662^2/4=1.183\ mm^2$, and the area of a rhombus is $2\times1.183\ mm^2=2.366\ mm^2$.

By obtaining the area of the rhombus through this process, the area of the semiconductor chip 100 constituting the wafer level chip scale package according to one or more embodiments of the present application can be obtained, and this calculation method can be equally applied to all verification examples below.

Table 1 below is a verification example comparing the prior art with a square structure and one or more embodiments of the present application with a rhombus structure when the number of solder balls is approximately 9.

TABLE 1

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 1(Square) | 9(3 × 3) | 0.2 | 0.2 | 0.1 | 1.2 | 1.2 | 1.440 | — |
| Example 1(Rhombus) | 9 | 0.2 | 0.2 | 0.1 | 1.262 | N/A | 1.364 | 94.729 |

Referring to Table 1, according to the prior art with the square structure, the semiconductor chip 1 having an area of approximately 1.440 $mm^2$ is required to arrange approximately 9 solder balls on the semiconductor chip, but according to one or more embodiments of the present application with the rhombus structure, the semiconductor chip 100 having an area of approximately 1.364 $mm^2$ is required to arrange approximately 9 solder balls on the semiconductor chip. Therefore, in the process of arranging approximately 9 solder balls on the semiconductor chip, one or more embodiments of the present application provide an effect of reducing the area of the semiconductor chip 100 by approximately 5.271% compared to the prior art.

Table 2 below is a verification example comparing the prior art with a square structure and one or more embodiments of the present application with a rhombus structure when the number of solder balls is approximately 16.

TABLE 2

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 2(Square) | 16(4 × 4) | 0.2 | 0.2 | 0.1 | 1.6 | 1.6 | 2.560 | — |
| Example 2(Rhombus) | 16 | 0.2 | 0.2 | 0.1 | 1.662 | N/A | 2.366 | 92.416 |

Referring to Table 2, according to the prior art with the square structure, the semiconductor chip 1 having an area of approximately 2.560 $mm^2$ is required to arrange approximately 16 solder balls on the semiconductor chip, but according to one or more embodiments of the present application with the rhombus structure, the semiconductor chip 100 having an area of approximately 2.366 $mm^2$ is required to arrange approximately 16 solder balls on the semiconductor chip. Therefore, in the process of arranging approximately 16 solder balls on the semiconductor chip, one or more embodiments of the present application provide an effect of reducing the area of the semiconductor chip 100 by approximately 7.584% compared to the prior art.

Table 3 below is a verification example comparing the prior art with a square structure and one or more embodiments of the present application with a rhombus structure when the number of solder balls is approximately 25.

TABLE 3

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 3(Square) | 25(5 × 5) | 0.2 | 0.2 | 0.1 | 2 | 2 | 4.000 | — |
| Example 3(Rhombus) | 25 | 0.2 | 0.2 | 0.1 | 2.062 | N/A | 3.642 | 91.043 |

Referring to Table 3, according to the prior art with the square structure, the semiconductor chip 1 having an area of approximately 4.000 $mm^2$ is required to arrange approximately 25 solder balls on the semiconductor chip, but according to one or more embodiments of the present application with the rhombus structure, the semiconductor chip 100 having an area of approximately 3.642 $mm^2$ is required to arrange approximately 25 solder balls on the semiconductor chip. Therefore, in the process of arranging approximately 25 solder balls on the semiconductor chip, one or more embodiments of the present application provide an effect of reducing the area of the semiconductor chip 100 by approximately 8.957% compared to the prior art.

Table 4 below is a verification example comparing the prior art with a square structure and one or more embodiments of the present application with a rhombus structure when the number of solder balls is approximately 36.

TABLE 4

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 4(Square) | 36(6 × 6) | 0.2 | 0.2 | 0.1 | 2.4 | 2.4 | 5.760 | — |
| Example 4(Rhombus) | 36 | 0.2 | 0.2 | 0.1 | 2.462 | N/A | 5.192 | 90.132 |

Referring to Table 4, according to the prior art with the square structure, the semiconductor chip 1 having an area of approximately 5.760 $mm^2$ is required to arrange approximately 36 solder balls on the semiconductor chip, but according to one or more embodiments of the present application with the rhombus structure, the semiconductor chip 100 having an area of approximately 5.192 $mm^2$ is required to arrange approximately 36 solder balls on the semiconductor chip. Therefore, in the process of arranging approximately 36 solder balls on the semiconductor chip, one or more embodiments of the present application provide an effect of reducing the area of the semiconductor chip 100 by approximately 9.868% compared to the prior art.

Table 5 below is a verification example comparing the prior art with a square structure and one or more embodiments of the present application with a rhombus structure when the number of solder balls is approximately 49.

TABLE 5

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 5(Square) | 49(7 × 7) | 0.2 | 0.2 | 0.1 | 2.8 | 2.8 | 7.840 | — |
| Example 5(Rhombus) | 49 | 0.2 | 0.2 | 0.1 | 2.862 | N/A | 7.016 | 89.485 |

Referring to Table 5, according to the prior art with the square structure, the semiconductor chip 1 having an area of approximately 7.840 $mm^2$ is required to arrange approximately 49 solder balls on the semiconductor chip, but according to one or more embodiments of the present application with the rhombus structure, the semiconductor chip 100 having an area of approximately 7.016 $mm^2$ is required to arrange approximately 49 solder balls on the semiconductor chip. Therefore, in the process of arranging approximately 49 solder balls on the semiconductor chip, one or more embodiments of the present application provide an effect of reducing the area of the semiconductor chip 100 by approximately 10.515% compared to the prior art.

Table 6 below is a verification example comparing the prior art with a square structure and one or more embodiments of the present application with a rhombus structure when the number of solder balls is approximately 100.

TABLE 6

| Type | Solder Ball count (number) | Ball size (mm) | Space (mm) | Edge (mm) | X (mm) | Y (mm) | Area ($mm^2$) | Area Ratio (%) |
|---|---|---|---|---|---|---|---|---|
| Comparative example 6(Square) | 100(10 × 10) | 0.2 | 0.2 | 0.1 | 4 | 4 | 16.000 | — |
| Example 6(Rhombus) | 100 | 0.2 | 0.2 | 0.1 | 4.062 | N/A | 14.132 | 88.326 |

Referring to Table 6, according to the prior art with the square structure, the semiconductor chip 1 having an area of approximately 16.000 $mm^2$ is required to arrange approximately 100 solder balls on the semiconductor chip, but according to one or more embodiments of the present application with the rhombus structure, the semiconductor chip 100 having an area of approximately 14.132 $mm^2$ is required to arrange approximately 100 solder balls on the semiconductor chip. Therefore, in the process of arranging approximately 100 solder balls on the semiconductor chip, one or more embodiments of the present application provide an effect of reducing the area of the semiconductor chip 100 by approximately 11.674% compared to the prior art.

As described above, according to one or more embodiments of the present application, there is an effect of providing a wafer level chip scale package with a rhombus shape that can reduce the chip size by approximately 5 to 12% compared to a conventional rectangular or square chip package.

In addition, there is an effect of providing a wafer level chip scale package with a rhombus shape that can still be manufactured using conventional semiconductor manufacturing equipment.

Although the wafer level chip scale package with a rhombus shape has been described with reference to the specific embodiments, it is not limited thereto. Therefore, it will be readily understood by those skilled in the art that various modifications and changes can be made thereto without departing from the spirit and scope of the present application defined by the appended claims.

What is claimed is:

1. A wafer level chip scale package with a rhombus shape comprising:

a semiconductor chip with a rhombus shape; and a solder ball array comprising a plurality of solder balls formed on one surface of the semiconductor chip, wherein among four interior angles of the semiconductor chip, two of the four interior angles facing each other in a short diagonal direction are approximately 120°, and two of the four interior angles facing each other in a long diagonal direction are approximately 60° the solder balls are arranged in a plurality of rows in the solder ball array, n solder balls are arranged on the short diagonal of the semiconductor chip, and in upper and lower regions of the short diagonal of the semiconductor chip, a number of solder balls in each row decreasing one by one until the number of solder balls becomes one from the n solder balls is alternately arranged.

2. The wafer level chip scale package of claim 1, wherein separation distances between adjacent solder balls constituting the solder ball array are the same.

3. The wafer level chip scale package of claim 2, wherein the semiconductor chip has a planar shape formed by two equilateral triangles, and the plurality of solder balls constituting the solder ball array are symmetrically arranged on the one surface of the semiconductor chip with respect to a short diagonal and a long diagonal of the semiconductor chip.

4. The wafer level chip scale package of claim 3, wherein a triangle formed by three line segments connecting three center points of three of the solder balls that are adjacent to each other is equilateral.

* * * * *